(12) United States Patent
Yoon et al.

(10) Patent No.: US 11,830,719 B2
(45) Date of Patent: Nov. 28, 2023

(54) LIGHT IRRADIATION DEVICE

(71) Applicant: UNILAM CO., LTD., Ulsan (KR)

(72) Inventors: Joo Young Yoon, Busan (KR); Eun Sik Kim, Busan (KR); Hong Chae Jung, Gyeongsangnam-do (KR); Se Hwi Park, Busan (KR); So Ree Kim, Ulsan (KR)

(73) Assignee: UNILAM CO., LTD., Ulsan (KR)

( * ) Notice: Subject to any disclaimer, the term of this patent is extended or adjusted under 35 U.S.C. 154(b) by 4 days.

(21) Appl. No.: 17/834,012

(22) Filed: Jun. 7, 2022

(65) Prior Publication Data
US 2022/0392760 A1    Dec. 8, 2022

(30) Foreign Application Priority Data
Jun. 7, 2021 (KR) .......... 10-2021-0073314

(51) Int. Cl.
*H01J 61/54*  (2006.01)
*H01J 61/30*  (2006.01)
*H01J 61/40*  (2006.01)

(52) U.S. Cl.
CPC .......... *H01J 61/547* (2013.01); *H01J 61/30* (2013.01); *H01J 61/40* (2013.01)

(58) Field of Classification Search
CPC .......... H01J 61/547; H01J 61/30; H01J 61/40; H01J 65/00–08; A61L 2/10
See application file for complete search history.

(56) References Cited

U.S. PATENT DOCUMENTS

| 2017/0186596 A1 | 6/2017 | Shinoda et al. | |
| 2022/0031879 A1* | 2/2022 | Nakamura | ............ H01J 65/046 |

FOREIGN PATENT DOCUMENTS

| JP | 2006040867 A | * | 2/2006 | ............ H01J 61/54 |
| JP | 2020068133 A | * | 4/2020 | |
| WO | WO-2013038859 A1 | * | 3/2013 | ............ H01J 61/54 |

* cited by examiner

*Primary Examiner* — Mariceli Santiago
(74) *Attorney, Agent, or Firm* — The PL Law Group, PLLC

(57) ABSTRACT

A light irradiation device according to an embodiment of the present disclosure has high light irradiation efficiency and cooling efficiency and can be reduced in size. The light irradiation device includes an excimer lamp including a light emitting tube that emits light, and a lamp electrode provided on an outside of the light emitting tube, and a case including a case body in which the excimer lamp is accommodated, a connection support provided at one side of the case body to be connected to the lamp electrode, and a case electrode provided at the other side of the case body to be in contact with a surface of the light emitting tube.

15 Claims, 8 Drawing Sheets

LIGHT IRRADIATION DEVICE

CROSS-REFERENCE TO RELATED APPLICATION(S) AND CLAIM OF PRIORITY

This application claims the benefit under 35 U.S.C. § 119 of Korean Patent Application No. 10-2021-0073314, filed on Jun. 7, 2021, in the Korean Intellectual Property Office, the entire disclosure of which is incorporated herein by reference for all purposes.

BACKGROUND

1. Field

The following description relates to a light irradiation device which has high light irradiation efficiency and cooling efficiency and is capable of being reduced in size and operated in real time.

2. Description of Related Art

Recently, light irradiation devices using ultraviolet light are used in various fields such as industry, environment, medical, and sterilization fields. Among light sources used in such light irradiation devices, an excimer lamp is one kind of lamp using dielectric barrier discharge. Here, the dielectric barrier discharge means discharge generated between two electrodes separated by an insulating dielectric, and due to the dielectric barrier discharge, a discharge gas enclosed in a light emitting tube is excited, and then light having a specific wavelength may be emitted in a process of gas molecules restoring their ground state. As such, the wavelength of light emitted by the excimer lamp varies depending on the type of the discharge gas enclosed in the light emitting tube, and the excimer lamp may be employed for various uses such as photowashing, air purification, surface modification, skin treatment, and sterilization depending on the varying wavelength of the light.

Typical excimer lamps include various types of excimer lamps, such as a single tube-type excimer lamp, a dual tube-type excimer lamp, an external electrode-type excimer lamp, and a quadrangular excimer lamp, and are installed in the light irradiation devices to emit light having a specific wavelength due to the dielectric barrier discharge.

Among the excimer lamps, the typical quadrangular excimer lamp will be described with reference to FIG. 1 as follows.

FIG. 1 is a schematic cross-sectional view illustrating a quadrangular excimer lamp according to the related art.

Referring to FIG. 1, the quadrangular excimer lamp according to the related art includes a light emitting tube 1, which has a discharge space for enclosing a discharge gas therein and has a quadrangular cross-section shape, and a pair of electrodes 2 and 3 which are provided on a top surface and a bottom surface of the light emitting tube 1 and to which a high voltage is applied.

Accordingly, a high-frequency and high-voltage power source is applied to the pair of electrodes 2 and 3 to generate dielectric barrier discharge, and due to the discharge, light is emitted from the light emitting tube 1. Here, depending on the wavelength of the emitted light, the excimer lamp is employed for various uses such as photowashing, air purification, surface modification, skin treatment, and removal of germs and viruses.

The excimer lamp emits light in a wavelength range of about 207 nm or about 222 nm of a UV-C region so as to remove germs and viruses. In particular, the wavelength range of about 207 nm or about 222 nm is classified as a Far UV-C region of the UV-C region. The light in the Far UV-C region is effective in removal of germs and viruses, and also harmless to human bodies due to the characteristics of cell-penetrating ability of the wavelength even when humans are exposed to the light.

However, when a spectrum of the UV-C light emitted from the typical excimer lamp is identified, the actually emitted light has a certain spectral narrow width, and a center wavelength thereof has the Far UV-C region, but a region excluding the center wavelength has a wavelength range of about 240 nm or more, i.e., about 240 nm to about 300 nm, thereby including a band spectrum having lower intensity of light than the center wavelength. Here, the light in the wavelength range of about 240 nm to about 300 nm is harmful to human bodies.

Thus, when the excimer lamp according to the related art is applied to a light irradiation device, a separate filter member needs to be installed in the light irradiation device so as to selectively block or reduce the light in the damaging wavelength range.

In addition, when the excimer lamp according to the related art is applied to a light irradiation device, a lead wire connected to a power supplier needs to be electrically connected to the excimer lamp so as to apply a power source to the pair of electrodes 2 and 3.

Therefore, the light irradiation device according to the related art has a limitation in miniaturization due to space secure for installing the lead wire which connects the power supplier to the excimer lamp in the light irradiation device. Moreover, during maintenance, the lead wire and/or the filter member need to be separated, and thus, the maintenance work is made complicated and inconvenient, and takes a long time.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

The disclosed embodiments are intended to provide a light irradiation device having improved light irradiation efficiency and cooling efficiency.

In addition, the disclosed embodiments are intended to provide the light irradiation device which is capable of being miniaturized and saved in manufacturing cost.

Moreover, the disclosed embodiments are intended to provide the light irradiation device which is capable of performing real-time sterilization and a lighting function together with the sterilization.

In one general aspect, there is provided a light irradiation device including: an excimer lamp including a light emitting tube that emits light, and a lamp electrode provided outside the light emitting tube; and a case including a case body, in which the excimer lamp is accommodated, a connection support provided at one side of the case body so as to be connected to the lamp electrode, and a case electrode provided at the other side of the case body so as to be in contact with a surface of the light emitting tube.

The connection support may be fixed on an inner surface of the case body and made of a conductive material.

The connection support may elastically and fixedly support the lamp electrode, or may detachably and fixedly support the lamp electrode.

The case electrode may be fixed to be in close contact with an inner surface of the case body, which opposes the connection support.

The case electrode may have a contact surface provided in a shape corresponding to a surface of the light emitting tube, and the contact surface may be provided as a reflective surface that reflects the light emitted from the light emitting tube.

The lamp electrode may be provided as an electrode layer disposed on a surface in a light irradiation direction among surfaces of the light emitting tube to have an opening exposing a portion of the surface of the light emitting tube.

The lamp electrode may be provided as an electrode member which has an opening exposing a portion of a surface in a light irradiation direction among surfaces of the light emitting tube and is attached on the surface of the light emitting tube.

The lamp electrode may be provided as an electrode layer or an electrode member provided in the form of a mesh or in the form of a plurality of crossing lines.

An open transmission unit may be disposed in one surface of the case body, which faces the lamp electrode.

The transmission unit may be provided with a filter that filters the light emitted from the light emitting tube.

The filter may filter the light so that the transmitted light has a wavelength of about 240 nm or less.

The transmission unit may be provided with a window through which the light emitted from the light emitting tube is transmitted and emitted to the outside.

The light emitting tube may have a discharge space therein and be provided in the form of a sealed tube having a cross-section in at least one of a circular, an oval, or a polygonal shape.

The light irradiation device according to an embodiment of the present disclosure may include a light source for lighting provided in the case body.

The light source for lighting may be operatively associated with the excimer lamp.

The light irradiation device according to an embodiment of the present disclosure may further include a detection sensor provided in the case body.

Other features and aspects will be apparent from the following detailed description, the drawings, and the claims.

Figure 1:
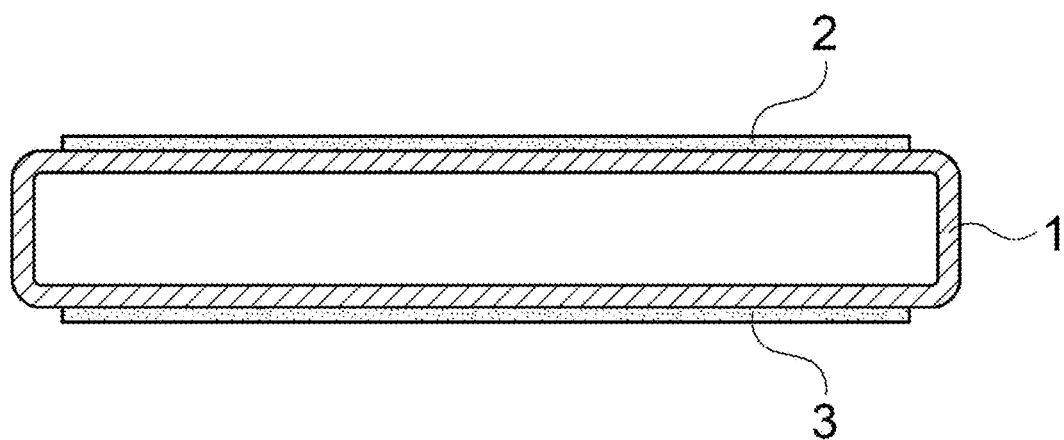
FIG. 1 is a schematic cross-sectional view illustrating a quadrangular excimer lamp according to the related art.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION OF THE EMBODIMENTS

Hereinafter, an embodiment of the present disclosure will be described with reference to the accompanying drawings. The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art.

Descriptions of well-known functions and constructions may be omitted for increased clarity and conciseness. Also, terms described in below are selected by considering functions in the embodiment and meanings may vary depending on, for example, a user or operator's intentions or customs. Therefore, definitions of the terms should be made on the basis of the overall context. The terminology used in the detailed description is provided only to describe embodiments of the present disclosure and not for purposes of limitation. Unless the context clearly indicates otherwise, the singular forms include the plural forms. It should be understood that the terms "comprises" or "includes" specify some features, numbers, steps, operations, elements, and/or combinations thereof when used herein, but do not preclude the presence or possibility of one or more other features, numbers, steps, operations, elements, and/or combinations thereof in addition to the description.

Figure 2:
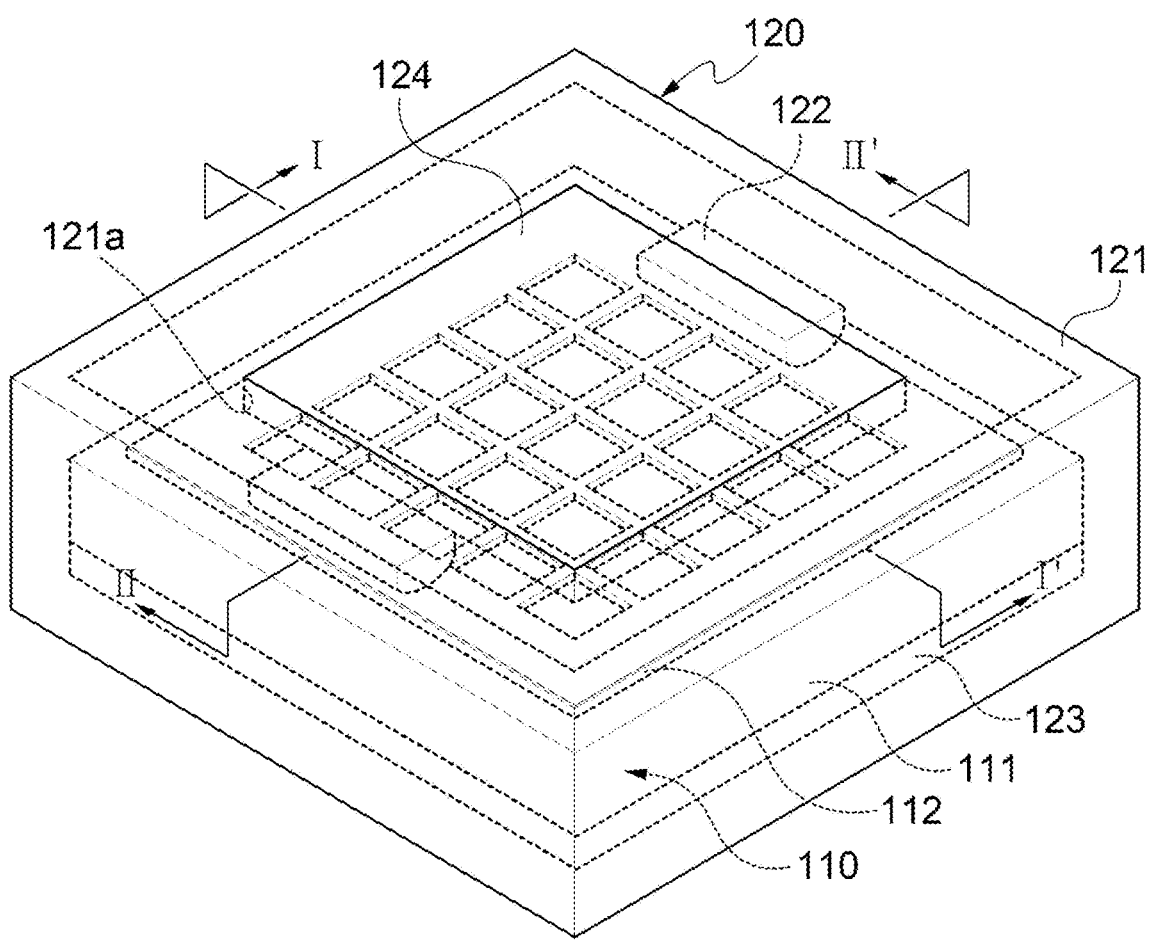
FIG. 2 is a schematic perspective view illustrating a light irradiation device according to an embodiment of the present disclosure.
Figure 3A:
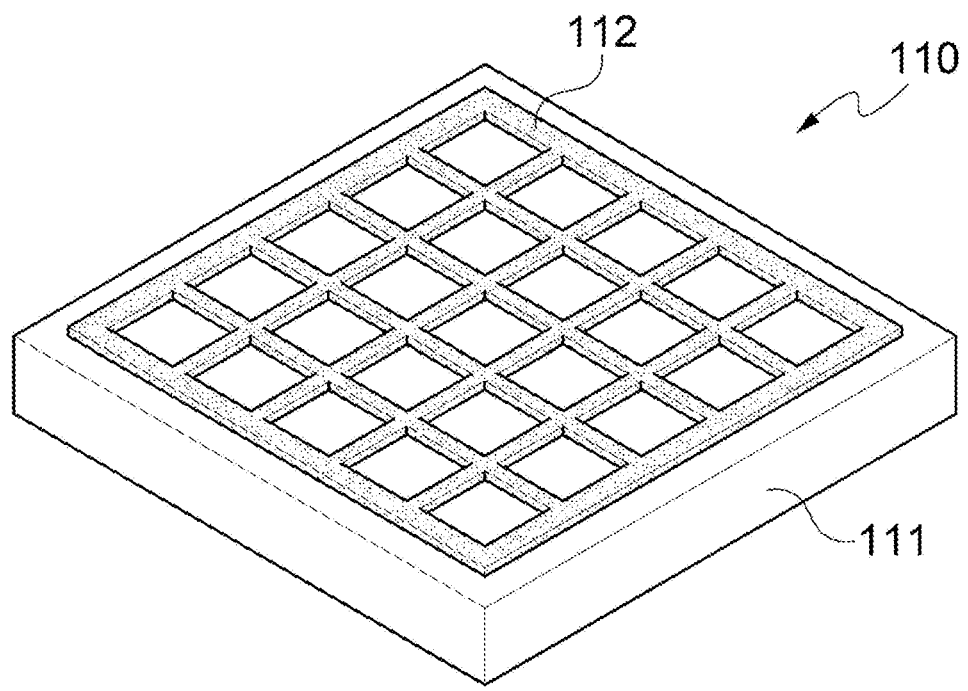
FIG. 3A is a schematic perspective view illustrating an excimer lamp in FIG. 2.
Figure 3B:
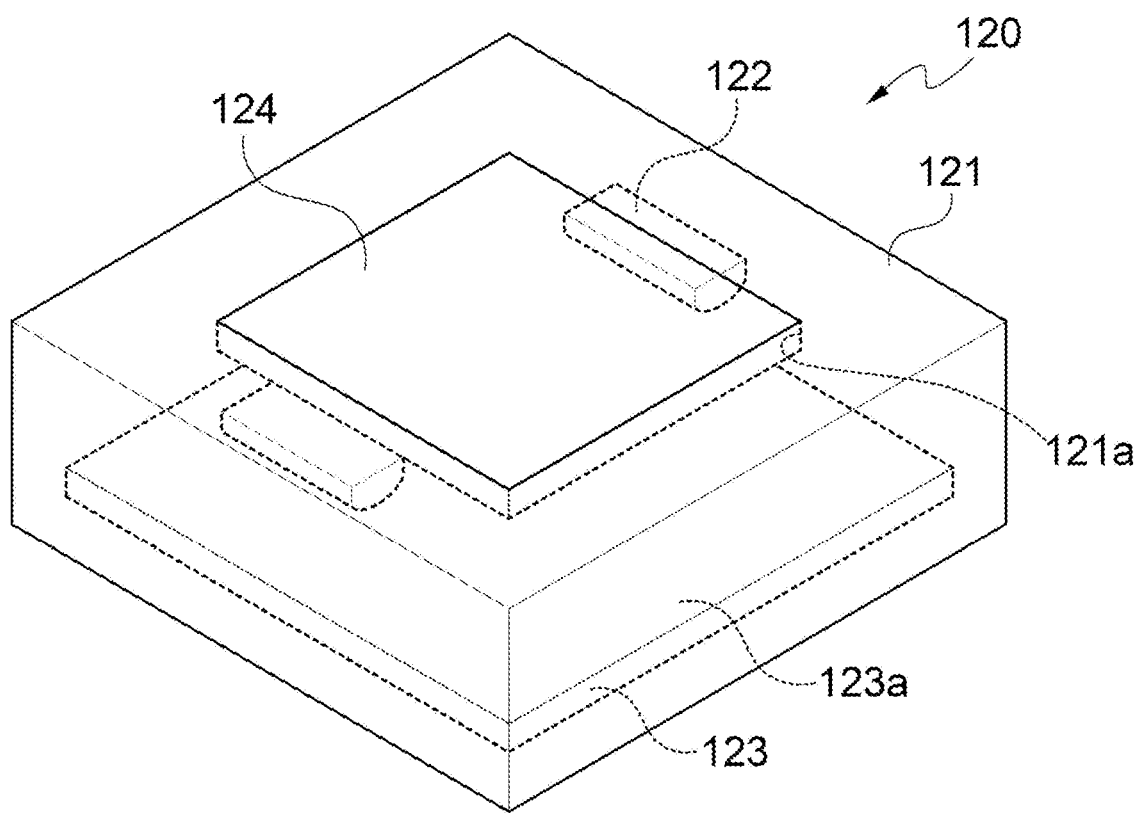
FIG. 3B is a schematic perspective view illustrating a case in FIG. 2.
Figure 3C:
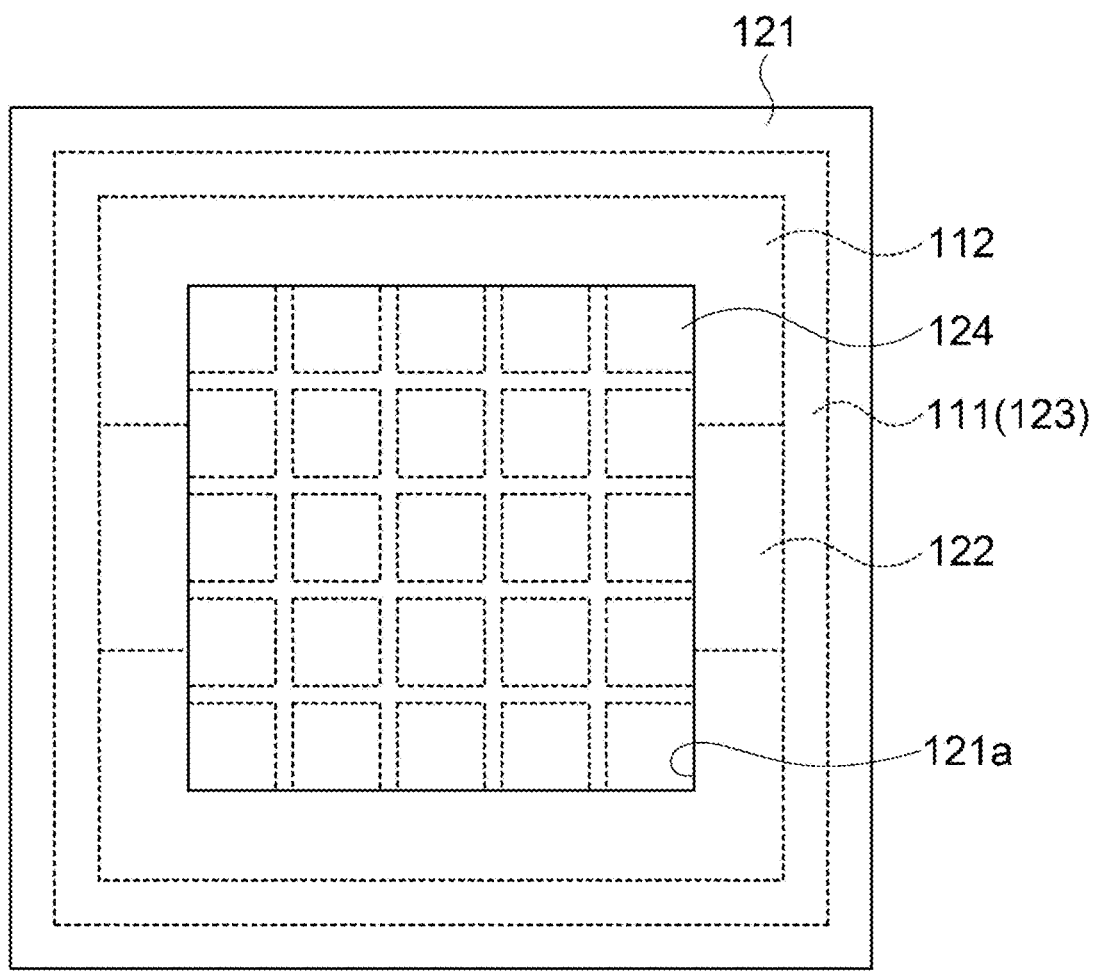
FIG. 3C is a plan view of FIG. 2.
Figure 3D:
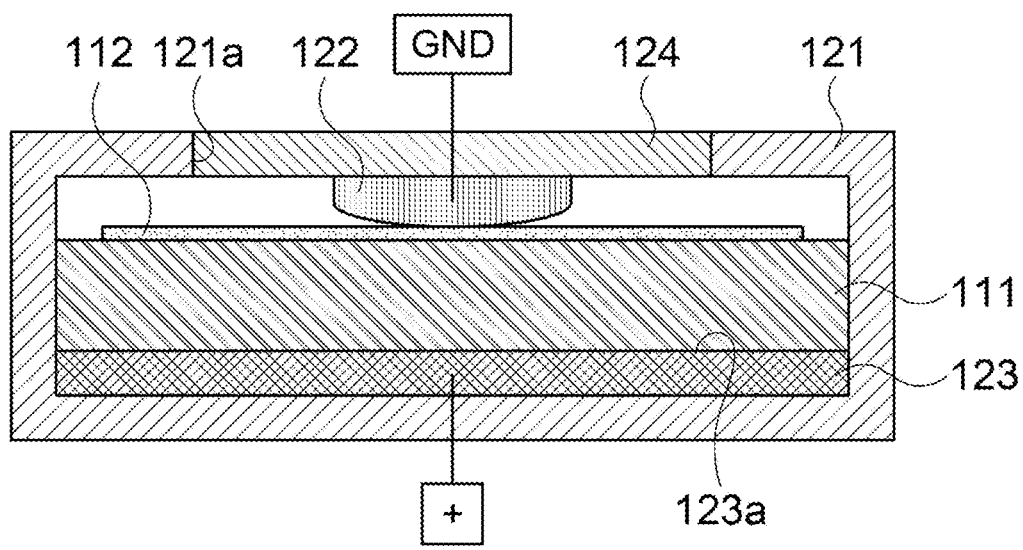
FIG. 3D is a cross-sectional view taken along a line I-I' in FIG. 2.
Figure 3E:
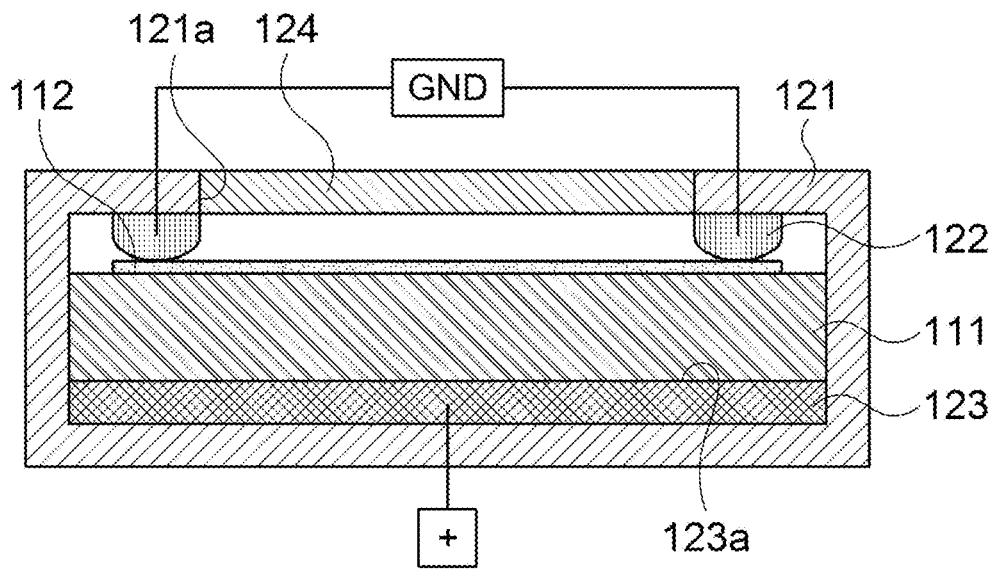
FIG. 3E is a cross-sectional view taken along a line II-II' in FIG. 2.

FIG. 2 is a schematic perspective view illustrating a light irradiation device according to an embodiment of the present disclosure. FIG. 3A is a schematic perspective view illustrating an excimer lamp in FIG. 2. FIG. 3B is a schematic perspective view illustrating a case in FIG. 2. FIG. 3C is a plan view of FIG. 2. FIG. 3D is a cross-sectional view taken along a line I-I' in FIG. 2. FIG. 3E is a cross-sectional view taken along a line II-II' in FIG. 2.

Referring to FIGS. 2 to 3E, a light irradiation device 100 according to an embodiment of the present disclosure may largely include an excimer lamp 110 that emits light, and a case 120 in which the excimer lamp 110 is accommodated.

The excimer lamp 110 may include a light emitting tube 111 having a discharge gas enclosed therein to emit the light when dielectric barrier discharge occurs, and a lamp electrode 112 provided on a top surface of the light emitting tube 111.

The case 120 may include a case body 121, in which the excimer lamp 110 is accommodated and which defines an outer appearance, a connection support 122 connected to the lamp electrode 112 of the excimer lamp 110, and a case electrode 123 that is in contact with the light emitting tube 111 of the excimer lamp 110.

More particularly, the connection support 122 may be fixed on an inner surface of the case body 121 and made of a conductive material. Here, the connection support 122 may elastically and fixedly support the lamp electrode 112 or may detachably and fixedly support the lamp electrode 112. In this embodiment, the connection support 122 is described as an elastic body made of a conductive material, but is not limited thereto, and have various structures, such as an elastic piece, an elastic clip, or hook, in which the connection support 122 is electrically connected to the lamp electrode 112 and also detachably and fixedly supports the lamp electrode 112.

The case electrode 123 may have a contact surface 123a having a shape corresponding to a surface in a direction opposite to the light irradiation direction among surfaces of the light emitting tube 111. That is, a top surface of the case electrode 123 may serve as the contact surface 123a to be in contact with a bottom surface of the light emitting tube 111, and thus the case electrode 123 together with the lamp electrode 112 may function as a pair of electrodes for the dielectric barrier discharge of the light emitting tube 111. The case electrode 123 may be fixed to be in close contact with an inner surface of the case body 121, which opposes the connection support 122. That is, when the connection support 122 is provided on an inner top surface of the case body 121, the case electrode 123 may be provided on an inner bottom surface of the case body 121.

A ground (GND) voltage may be connected to the connection support 122, and a plus (+) voltage may be connected to the case electrode 123. Accordingly, when the voltages are applied to the connection support 122 and the case electrode 123, the light may be emitted from the light emitting tube 111 through the dielectric barrier discharge by the lamp electrode 112 and the case electrode 123.

Here, the contact surface 123a of the case electrode 123 may function as a reflective surface that reflects the light emitted from the light emitting tube 111. Thus, the light reflected through the contact surface 123a may be introduced into the light emitting tube 111 and then emitted to the opposite side to improve the light irradiation efficiency of the excimer lamp 110. In addition, in this embodiment, the case electrode 123 may have a quadrangular structure corresponding to the light emitting tube 111 having a quadrangular structure, and thus the contact surface 123a may reflect the light in a flat form to improve light uniformity. Moreover, the case electrode 123 may serve as a medium that transfers, through the contact surface 123a, heat generated from the light emitting tube 111 toward the case body 121 to be emitted to the outside to effectively cool the heat generated when the light emitting tube 111 emits the light.

The lamp electrode 112 of the excimer lamp 110 may have an opening exposing a portion of a surface in the light irradiation direction among the surfaces of the light emitting tube 111. That is, the light emitted from the light emitting tube 111 may be emitted to the outside through the opening of the lamp electrode 112. The lamp electrode 112 may be provided as an electrode layer formed on the surface of the light emitting tube 111. For example, the lamp electrode 112 may be manufactured as an electrode layer by patterning the conductive material on the surface of the light emitting tube 111. Here, the lamp electrode 112 may be formed in the form of a mesh or in the form of a plurality of crossing lines, but is not limited thereto, and various structures, which are capable of being electrically connected to the connection support 122 and have the opening to allow the light to be emitted from the light emitting tube 111, are applicable. In addition, the shape of the lamp electrode 112 may have a shape designed to recognize various expressions and signs, etc., when the light irradiation device is seen from the outside.

The lamp electrode 112 may be provided as an electrode member attached on the surface of the light emitting tube 111. That is, the lamp electrode 112 may be separately manufactured as the electrode member by using a conductive material having the form of a mesh or the form of a plurality of crossing lines, and then the electrode member may be attached on the surface of the light emitting tube 111 to replace the electrode layer described above.

An open transmission unit 121a may be disposed in one surface of the case body 121, and thus the light emitted from the light emitting tube 111 may be emitted to the outside through the transmission unit 121a. A filter 124 may be provided in the transmission unit 121a to filter the light emitted from the light emitting tube 111 so that the filtered light is emitted to the outside. Here, the filter 124 may filter the light so that the transmitted light has a wavelength of about 240 nm or less. In addition, depending on the use, a short pass filter, a long pass filter, a band pass filter, a density filter, or the like may be applied as the filter 124. That is, the filter 124 may adjust an intensity of the transmitted light (UV light) so that the transmitted light has a wavelength of about 240 nm or less. Accordingly, the light irradiation device according to this embodiment may finally select and emit the light having the wavelength of about 240 nm or less, which is harmless to and safe for human bodies.

When the light filtration by the filter 124 is unnecessary according to the use, the transmission unit 121a may be provided with a window, which is made of a material allowing transmission of light, instead of the filter. Here, the window may not be installed, but may be provided to protect the excimer lamp 110, etc., provided in the case body 121.

Figure 4:
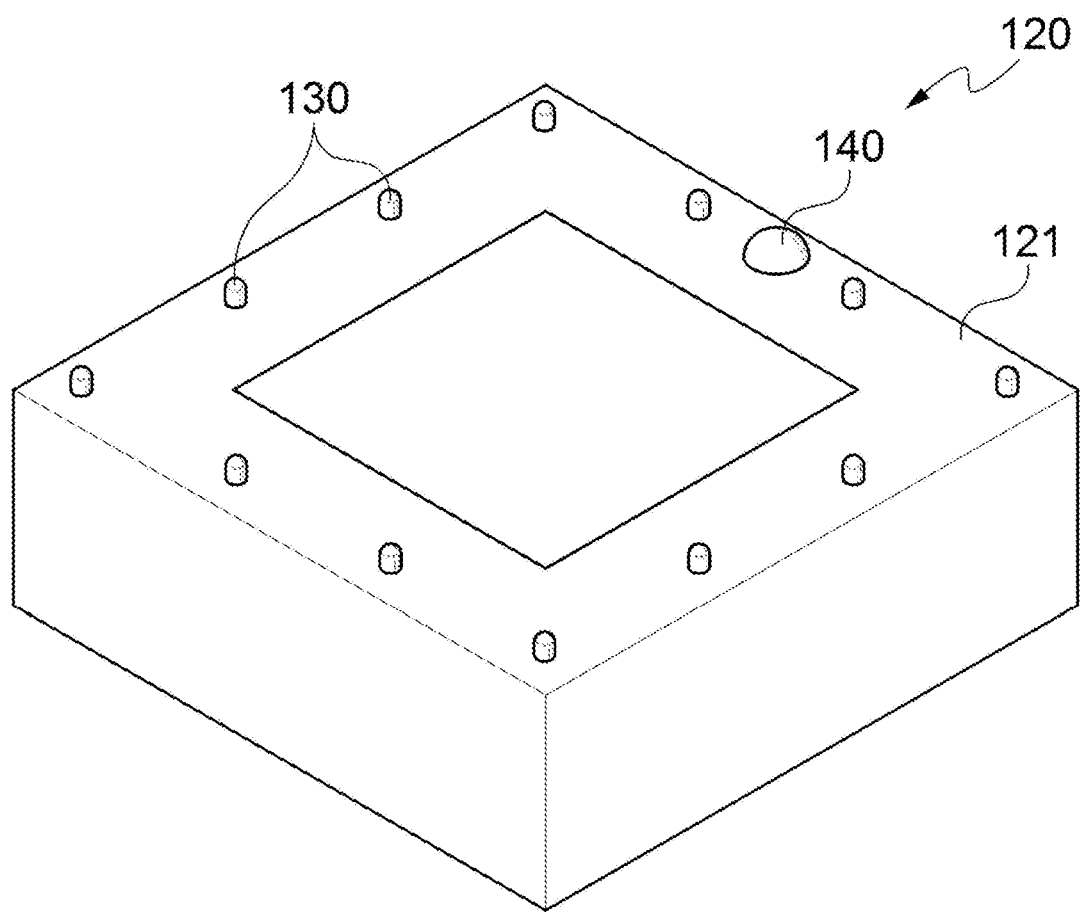
FIG. 4 is a schematic perspective view illustrating a light irradiation device according to another embodiment of the present disclosure.

FIG. 4 is a schematic perspective view illustrating a light irradiation device according to another embodiment of the present disclosure.

Referring to FIG. 4, the light irradiation device according to another embodiment of the present disclosure may also include a case 120 for accommodating an excimer lamp that emits light, similar to the embodiment described above.

However, the light irradiation device according to this embodiment may further include a light source 130 for lighting provided in the case 120. More particularly, at least one or more light sources 130 for lighting may be provided at one side of an outer surface in a light irradiation direction of a case body 121, i.e., the outer surface in which a transmission unit is disposed, so that the excimer lamp emits light for exterior lighting while emitting light for sterilization. When a power source is supplied to the excimer lamp, the power source is simultaneously supplied to the light source 130 for lighting so that the light source 130 for lighting is operatively associated with the excimer lamp. Here, an LED or the like may be applied as the light source 130 for lighting, but is not limited thereto, and various types of light sources are applicable.

In addition, the light irradiation device according to this embodiment may further include a detection sensor 140 provided in the case 120. More particularly, the detection sensor 140 may be provided at one side of the outer surface in the light irradiation direction of the case body 121, i.e., the outer surface in which the transmission unit is disposed. Accordingly, the light irradiation device according to this embodiment may be controlled to emit light in real time when the detection sensor 140 detects a sterile object, i.e., only when the irradiation with light is necessary, thereby preventing the power waste and stretching the entire lifetime of the excimer lamp. That is, when the detection sensor 140 detects an external movement or the like, the excimer lamp may be switched on and simultaneously, the light source 130 for lighting may be switched on, and when an external movement or the like is not detected for a predetermined time, the excimer lamp and the light source 130 for lighting may be switched off. Here, various types of detection sensors, such as a sensor for detecting an operation such as movement or a sensor for detecting heat or ultrasound, may be applied as the detection sensor 140.

In an embodiment of the present disclosure, the excimer lamp may be provided as the quadrangular light emitting tube, but is not limited thereto, and the light emitting tube may be provided in the form of the sealed tube having various cross-section shapes such as a circular, an oval, or a polygonal shape, while having the discharge space in which a discharge gas is enclosed.

Here, the shapes of the lamp electrode and the connection support may be changed corresponding to the varying shape of the light emitting tube of the excimer lamp. In particular, with the varying the shape of the light emitting tube, the case electrode may have the contact surface in the shape corresponding to the surface of the light emitting tube to efficiently reflect the light emitted from the light emitting tube and effectively dissipate the heat generated from the light emitting tube.

According to embodiments of the present disclosure, the electrical connection of the excimer lamp may be performed without the separate lead wire and the power supply may be achieved only with the single electrode provided in the excimer lamp to miniaturize the light irradiation device and save the manufacturing costs of the light irradiation device.

According to embodiments of the present disclosure, the heat generated from the light emitting tube may be effectively dissipated to the case side through the case electrode to improve the cooling efficiency and the performance of the light irradiation device.

According to embodiments of the present disclosure, the portion of the light emitted from the light emitting tube may be emitted by being reflected through the case electrode to improve the light efficiency and the light uniformity of the light irradiation device.

Moreover, according to embodiments of the present disclosure, the real-time sterilization may be performed to efficiently utilize the power source and perform the lighting function together with the sterilization.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A light irradiation device comprising:
   an excimer lamp comprising a light emitting tube configured to emit light, and a lamp electrode provided outside the light emitting tube; and
   a case comprising a case body in which the excimer lamp is accommodated, a connection support provided at one side of the case body so as to be connected to the lamp electrode, and a case electrode provided at an inner bottom surface of the case body so as to be in contact with a surface of the light emitting tube,
   wherein the connection support is made of a conductive material so as to be electrically connected to the lamp electrode,
   wherein the connection support is fixed on an inner surface of the case body, and
   the connection support elastically and fixedly supports the lamp electrode.

2. The light irradiation device of claim 1, wherein the case electrode is fixed to be in close contact with an inner surface of the case body, which opposes the connection support.

3. The light irradiation device of claim 1, wherein the case electrode has a contact surface provided in a shape corresponding to the surface of the light emitting tube.

4. The light irradiation device of claim 3, wherein the contact surface is provided as a reflective surface configured to reflect the light emitted from the light emitting tube.

5. The light irradiation device of claim 1, wherein the lamp electrode is provided as an electrode layer disposed on a surface in a light irradiation direction among surfaces of the light emitting tube to have an opening exposing a portion of the surface of the light emitting tube.

6. The light irradiation device of claim 5, wherein the lamp electrode is provided in the form a mesh or in the form of a plurality of crossing lines.

7. The light irradiation device of claim 1, wherein the lamp electrode is provided as an electrode member which has an opening exposing a portion of a surface in a light irradiation direction among surfaces of the light emitting tube and is attached on the surface of the light emitting tube.

8. The light irradiation device of claim 1, wherein an open transmission unit is disposed in one surface of the case body, which faces the lamp electrode.

9. The light irradiation device of claim 8, further comprising a window which is provided in the transmission unit and through which the light emitted from the light emitting tube is transmitted and emitted to the outside.

10. The light irradiation device of claim 1, wherein the light emitting tube has a discharge space therein and is provided in the form of a sealed tube having a cross-section in at least one of a circular, an oval, or a polygonal shape.

11. The light irradiation device of claim 1, further comprising a light source for lighting provided in the case body.

12. The light irradiation device of claim 11, wherein the light source for lighting is operatively associated with the excimer lamp.

13. A light irradiation device comprising:
   an excimer lamp comprising a light emitting tube configured to emit light, and a lamp electrode provided outside the light emitting tube;
   a case comprising a case body in which the excimer lamp is accommodated, a connection support provided at one side of the case body so as to be connected to the lamp electrode, and a case electrode provided at an inner bottom surface of the case body so as to be in contact with a surface of the light emitting tube, wherein the connection support is made of a conductive material so as to be electrically connected to the lamp electrode, and an open transmission unit is disposed in one surface of the case body, which faces the lamp electrode; and
   a filter provided in the transmission unit to filter the light emitted from the light emitting tube.

14. The light irradiation device of claim 13, wherein the filter filters the light so that the transmitted light has a wavelength of about 240 nm or less.

15. A light irradiation device comprising:
   an excimer lamp comprising a light emitting tube configured to emit light, and a lamp electrode provided outside the light emitting tube;
   a case comprising a case body in which the excimer lamp is accommodated, a connection support provided at one side of the case body so as to be connected to the lamp electrode, and a case electrode provided at an inner bottom surface of the case body so as to be in contact with a surface of the light emitting tube, wherein the connection support is made of a conductive material so as to be electrically connected to the lamp electrode; and a detection sensor provided in the case body.

* * * * *